United States Patent [19]

Klesius

[11] Patent Number: 5,290,501
[45] Date of Patent: Mar. 1, 1994

[54] METHOD OF FORMING CARDBOARD TAMPON APPLICATORS HAVING A DOME-SHAPED FORWARD TIP

[75] Inventor: Allan W. Klesius, Wynnewood, Pa.

[73] Assignee: Playtex Family Products Corporation, Samford, Conn.

[21] Appl. No.: 886,119

[22] Filed: May 20, 1992

[51] Int. Cl.⁵ .............................................. B29C 53/08
[52] U.S. Cl. ................................... 264/322; 264/295; 264/296; 264/339; 604/14
[58] Field of Search ............... 264/296, 257, 299, 320, 264/322, 324, 339, 295; 604/14, 15

[56] References Cited

U.S. PATENT DOCUMENTS

| | | |
|---|---|---|
| 912,285 | 2/1909 | Collins . |
| 1,089,402 | 3/1914 | Downing . |
| 1,989,015 | 1/1935 | McKellip . |
| 3,198,092 | 8/1965 | Koran . |
| 3,204,635 | 9/1965 | Voss et al. . |
| 3,433,225 | 3/1969 | Voss et al. . |
| 3,753,437 | 8/1973 | Hood et al. . |
| 3,758,357 | 9/1973 | Akerson et al. ............... 264/324 |
| 3,821,350 | 6/1974 | Sughane ........................ 264/259 |
| 3,826,178 | 7/1974 | Taylor . |
| 3,895,634 | 7/1975 | Berger et al. . |
| 4,302,174 | 11/1981 | Hinzmann ..................... 264/296 |
| 4,412,833 | 11/1983 | Wiegner et al. ............... 604/14 |
| 4,453,925 | 6/1984 | Decker ........................... 604/14 |
| 4,508,531 | 4/1985 | Whitehead ..................... 604/14 |
| 4,551,126 | 11/1985 | Johnson, Jr. et al. ......... 493/453 |
| 4,650,459 | 3/1987 | Sheldon ......................... 604/15 |
| 4,755,164 | 7/1988 | Hinzmann ..................... 493/288 |
| 5,087,239 | 2/1992 | Beastall et al. ................ 604/14 |

Primary Examiner—Jan H. Silbaugh
Assistant Examiner—Mathica Vargot
Attorney, Agent, or Firm—Abelman Frayne & Schwab

[57] ABSTRACT

A method for forming a tampon applicator having a dome shape forward end, in which the stability of the petal tips to maintain their closure, is enhanced. During the manufacture of the tampon barrel, the petals which collectively form the dome shape tip are sprayed with a predetermined amount of moisture prior to their being presented to the heated tip forming die. It has been observed that the addition of moisture prior to petal tip formation counteracts the tendency of the petal tips to thereafter move towards their opened condition.

11 Claims, 3 Drawing Sheets

METHOD OF FORMING CARDBOARD TAMPON APPLICATORS HAVING A DOME-SHAPED FORWARD TIP

This invention relates to tampon applicators which have a dome-shape forward end and are intended for the storage and ejection of tampon pledgets, and more particularly to the method of fabricating the petals so that the individual petals which form the tip have increased stability to maintain tip closure over prolonged periods of storage.

BACKGROUND OF THE INVENTION

Tampon applicators which include a pair of telescoping cylinders are well known in the art. For example, Berger, U.S. Pat. No. 3,895,634, assigned to the assignee of the subject application, and Voss U.S. Pat. No. 3,433,225 typically show such applicators in Which the pledget is initially stored in the forward end of a cylindrical barrel. A lesser diameter plunger is telescopingly contained within the rear end of the barrel, such that the forward end of the plunger abuts the rear end of the pledget. Advantageously, the forward end of the barrel, which is inserted in the vagina prior to tampon injection, includes a smooth, dome-shaped end for user comfort. When the user then urges the plunger against the rear end of the pledget, the pledget is moved forwardly in the barrel, opening up the petals which form the dome-shape forward end of the barrel, as the pledget is ejected from the barrel. Following the full ejection of the tampon pledget, the petals then return towards their original closed position so as to comfortably remove the applicator from the body orifice.

Such tampon applicators are conventionally manufactured either of a suitable plastic composition, which is typically ejection molded, or from cardboard. In view of environmental concerns, cardboard applicators, which are water degradable or water dispersible, are increasingly desirable.

After such tampon applicators are fully assembled at the manufacturing location and shipped to the ultimate retail outlet, there is usually a prolonged duration of time between original manufacture and use. It has been observed that during this period there is a tendency of the individual cardboard petals forming the tip to open somewhat. The degree to which the petals open is referred to as petal tip stability. It is believed that this partial opening after being formed into their curved dome-shaped configuration is due to the memory of the cardboard which tends to urge the petals towards their initial open condition.

If the petal tips are not sufficiently stable, their premature opening prior to pledget ejection can result in an undesirable and oftentimes unacceptably uncomfortable insertion. Accordingly, it is desirable to effectively maintain the petals of the dome tip in a formed position prior to the user urging the telescoping plunger forward to intentionally eject the pledget through the dome shape forward tip of the barrel.

While various techniques have previously been proposed for modifying the forward end of dome-shaped cardboard applicators, none have been found to achieve the requisite increased stability in accordance with the other desirable applicator parameters. Hence, the increased stability achieved by the instant invention can be combined with other techniques for reduced ejection force and cardboard petal tip shaping so as to advantageously provide a tampon applicator tip construction which a) may be readily formed to its desired configuration, b) experiences a sufficiently low ejection pressure for ease of consumer use, and c) provides a high degree of petal tip stability for maintaining the tip configuration from the time of manufacture to the time of use. For example, my method for increased tip stability may be used in conjunction with the method for reducing the force for ejecting the tampon pledget through a petal tip applicator, as is the subject of Rejai U.S. patent application Ser. No. 07/886,114 filed on even date herewith and assigned to the assignee of the instant application. Other petal tip forming techniques which may be practiced in conjunction with the instant invention are disclosed in Wiegner, et al. U.S. Pat. No. 4,412,833 and Beastall et al. U.S. Pat. No. 4,087,239 which provide an indented circumferential groove (which can take the form of slots or perforations in Beastall) at the base of the cardboard petals to provide a hinge region for the bending of the petals. Such a hinge had also been disclosed in aforementioned Voss et al. U.S. Pat. No. 3,433,225. The petal tips may also include a series of transverse score or relief lines along the length of the cardboard petals to facilitate their bending into a round tip as shown in Whitehead U.S. Pat. No. 4,508,531 and Decker U.S. Pat. No. 4,453,925.

Further, recognizing that some variations are to be expected in the mass production of tampon applicators, as for example resulting from the characteristics of the cardboard or tip shaping, the enhanced petal tip stability provided by my invention, insures that appropriate performance will be achieved within the anticipated range of product manufacturing variations.

SUMMARY OF THE INVENTION

In accordance with the present invention, the petals, referred to as petal tips also are moistened somewhat, as by spraying, prior to their being shaped into their final curved dome-shaped configuration, as by a heated die. It has been determined that such spraying, which can be primarily water at ambient temperature, is an effective Way of significantly increasing the tip stability Without appreciably adding to the manufacturing time or cost. The degree of increased stability achieved by my invention may be measured by determining the gap which occurs between the forward ends of opposed petals. An increase in this gap after initial manufacture is a function of tip openings. It has been determined that a reduction at least in the order of 20 per cent is obtained in accordance with the instant invention.

It is accordingly a primary object of my invention to provide a method of forming a tampon applicator tube having a dome-shape forward end, which exhibits improved tip stability following its initial manufacture.

A further object is to provide such a method for forming a tampon applicator tube in which the tendency of the individual petals to open up is inhibited by spraying moisture on the petals prior to their shaping in a heated die.

Another object of my invention is to provide a cardboard tampon applicator having a dome shape tip in which the petals experience a high degree of stability, and a sufficiently low pledget ejection force.

These as well as other objects of my invention will now be further described and illustrated by reference to the accompanying drawings in which:

DESCRIPTION OF THE PREFERRED EMBODIMENTS

Figure 1:
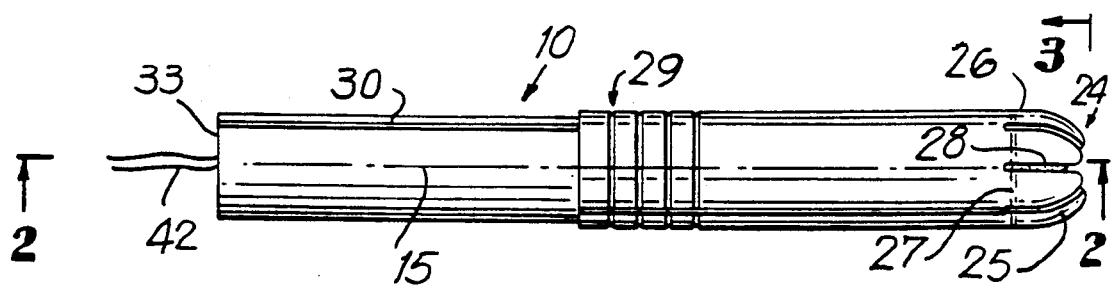
FIG. 1 is a side view of an assembled tampon applicator, including the pledget contained therein, constructed in accordance with my invention.
Figure 2:
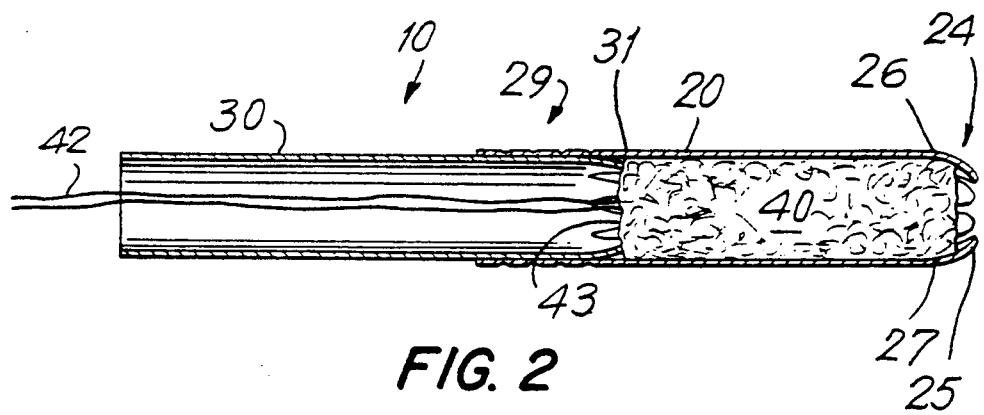
FIG. 2 is a cross-sectional view of the tampon applicator assembly shown in FIG. 1.

Referring initially to FIGS. 1-4, the tampon applicator assembly 10 includes a barrel or barrel member 20 and plunger 30 telescopingly contained within the rear end region of the barrel 20. A tampon pledget 40, which may partake of various known prior art pledget constructions, such as for example that shown in aforementioned Berger U.S. Pat. No. 3,895,634, is initially positioned within the forward end of the assembled barrel or barrel member 20. A withdrawal string 42 extends outwardly through the central portion of the plunger 30 for subsequent removal of the pledget from the user's body after ejection from the applicator assembly, and removal of the applicator from the user's body. The forward end 31 of the plunger typically abuts the rear end 43 of the pledget for moving the pledget forward, in the conventional manner so as to eject the pledget 40 from the forward end of the barrel.

The barrel 20 includes a dome shaped forward end 24 which is provided for more comfortable insertion of the applicator. The dome end is typically shown as comprising six individual petals 25 which are inwardly folded about their base region 26. Although six petals are shown a different number of petals may be employed, as is well known in the art. To aid in the inward folding of the petals a circumferential groove, shown as 27, may be provided around the inward surface at the petal base region. The groove 27, which is preferably embossed on the blank while it is in its flat state may preferably be formed by a pair of complementary members (not shown), which contact opposite surfaces of the flat blank prior to being formed into the barrel. One such member includes a circumferential projection corresponding to the groove to be formed at the base region. The other has a complementary circumferential recess. The coaction of the two members crush the fibers at the petal base region, thereby providing a hinge point to facilitate inward bending of the petals to their required dome configuration. Alternative)y, the groove may be formed on the outside of the cylindrical barrel, or the groove may be omitted.

Figure 4:
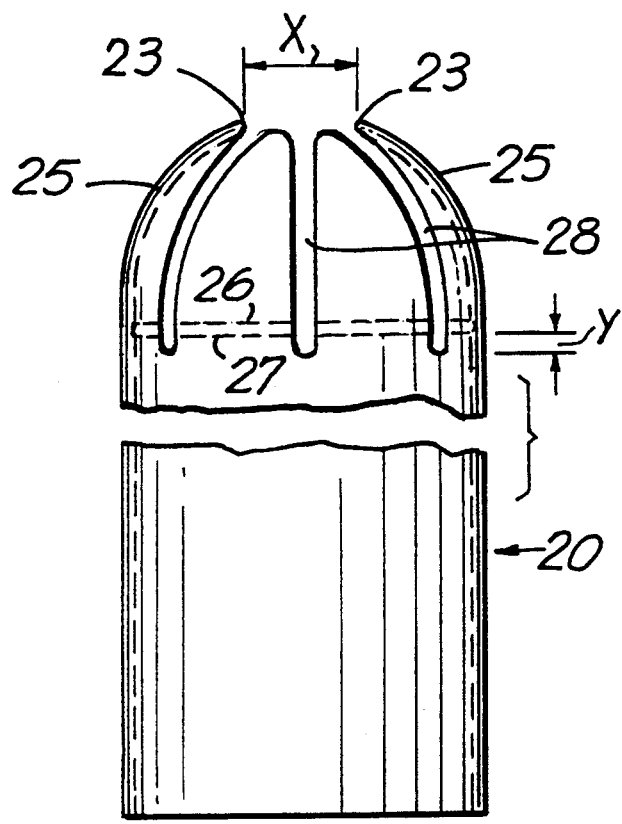
FIG. 4 is an enlarged side view of the frontal portion of the barrel showing the individual petals in greater detail.

It is preferable for the radial slits 28 between the sides of the petals 25 to extend somewhat below the base region 26 of the petals and the circumferential groove 27. Advantageously, this allows for tolerances with respect to anticipated manufacturing variations of the groove. The circumferential groove 27 is in the location not below the terminus of the radial slits 28. This displacement Y as shown in FIG. 4, (and as also shown in FIG. 4 of the aforementioned Ser. No. 07/886,114) between the groove 27 and lower terminus of slits 28 provides a region for the radial movement or bending of the petals 25 at the base region.

A finger grip section 29 is advantageously provided at the rear end of the barrel so as to facilitate the user's grasping and maintaining the applicator during pledget ejection, particularly if the outer surface of the applicator is made smooth to aid in comfortable applicator insertion. As is well known in the art, the fingergrip may be formed by a plurality of score lines, such as for example typically shown in aforementioned Wiegner et al. U.S. Pat. No. 4,412,833, or Jaycox U.S. Pat. No. 3,696,812. Although eight score lines are shown in FIG. 1, other numbers may be used, depending upon such factors as the thickness and smoothness of the cardboard forming the barrel 20.

Figure 3:
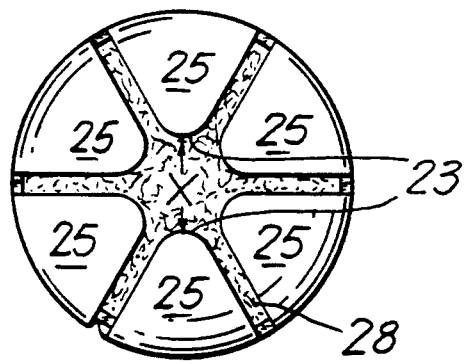
FIG. 3 is an enlarged end view of the tampon applicator assembly, in the direction of arrows 3—3 as shown in FIG. 1.

Reference is now made to the enlarged end view of FIG. 3 which shows the forward ends 23 of opposed frontal petals 25 separated by a gap or distance X. Distance X will have a predetermined range in order to insure proper petal tip stability. That is, should the petals tend to open up about their base region 26 the gap X between opposed petals will correspondingly increase. Accordingly, any increase in distance X correlates to the degree of petal tip opening, or its stability.

Figure 5:
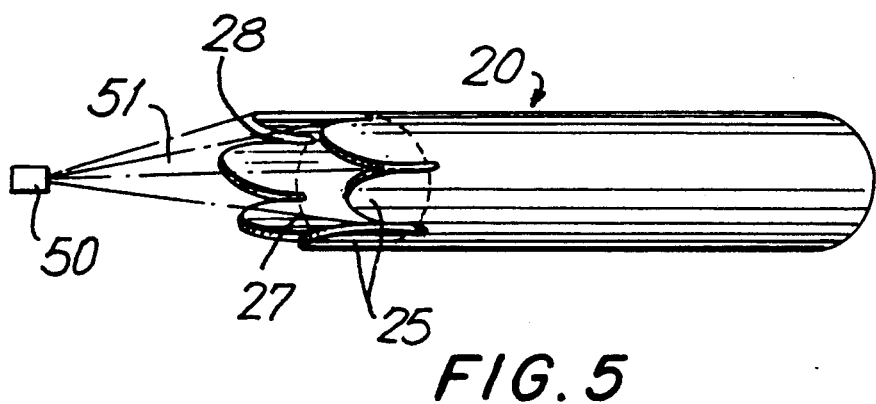
FIG. 5 shows the manner in which the moisture may be sprayed on the inner petal surfaces prior to their fabrication into the dome tip.

Reference is made to FIG. 5 which diagrammatically shows nozzle 50 directing a spray of moisture 51 over at least the forward end and a major portion of one or more surfaces of each of the petals. The spray is preferably against the inner surfaces of the petals 25. Alternatively, the moisture may be similarly applied to the outer surfaces of the petals, or both the inner and outer surfaces, by a suitable location of nozzles 50 (not shown) Moisture spray 51 may be primarily water but may include a small amount of a germicide such as hydrogen peroxide. The water temperature may be ambient, typically in the range of 75 to 80 degrees Fahrenheit. In practicing my invention in conjunction with typical commercial cardboard tampon applicator barrels, approximately 0.02 to 0.03 grams of moisture may be sprayed over the forward end of each barrel prior to forming the dome-shape tip.

Figure 6:
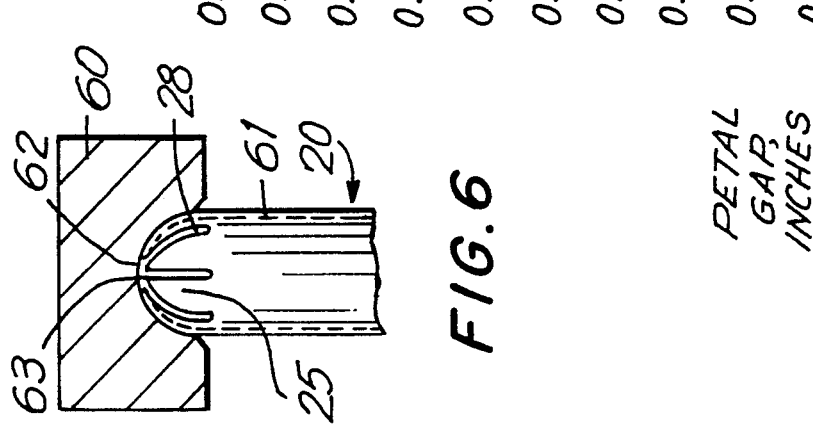
FIG. 6 shows the production tooling that may typically be used for thereafter shaping the moistened petals into the dome-shaped tip.

While the moisture is still present on the surface of the petal tips 25, the petals are then immediately presented into the inner concave surface of a forming tool or die 60, such shown in FIG. 6. Forming tool 60 may preferably be heated, in the order of 350 degrees Fahrenheit to aid in the fabrication of the tip, with the enhanced stability being achieved by the drying out of the moisture applied by nozzle assembly 50. During tip formation an inner mandrel 61, which may not be independently heated, is inserted within the barrel 20. Mandrel 61 has a forward curved end which is complementary to the concavity 63 of the heated forming tool 60. Naturally, the amount, temperature and characteristics of the moisture applied, as well as the temperature of the forming die 60 and the dwell time of the petal tips 25 in between forming die 60 and mandrel 61 may be adjusted in accordance with the characteristics of the particular cardboard used and other parameters of the tampon barrel 20.

Further additional intermediary steps may be practiced between that shown in FIGS. 5 and 6 to controllingly reduce the tampon pledget ejection force, as is the subject matter of aforementioned Rejai U.S. Ser. No. 07/886,114 filed on even date herewith.

Figure 7:
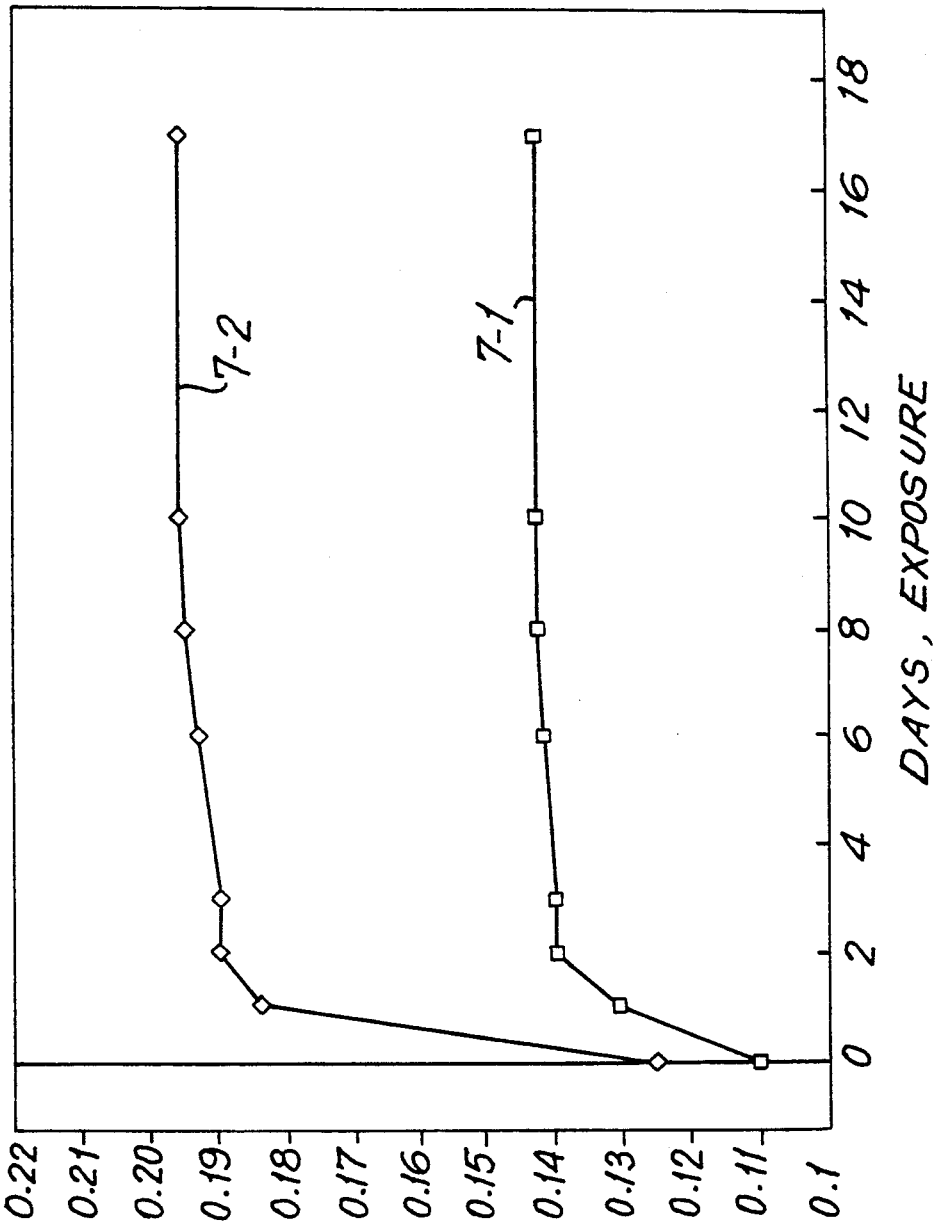
FIG. 7 graphically shows the increased stability which has been obtained in conjunction with barrels made according to the preferred method of my invention.

Referring now to FIG. 7, measurements were taken of a laminated cardboard barrel in which the inner ply is approximately 0.0135 inches and the outer ply is formed of 0.0018 inch wax coated KVP to provide the requisite smoothness and whiteness. Six petals are shown for with each petal being approximately between 0.340 and 0.440 inches long. The radial slit 28, shown in FIG. 3 between adjacent petals is approximately 0.024 inches wide and may extend 0.02 inches beyond the bottom extreme of the circumferential hinge 27, (i.e. 0.020 to 0.030 inches below the center line of the hinge 27 as described in aforementioned Ser. No. 07/886,114). This groove or hinge 27 is typically 0.020 inches wide and 0.007 to 0.010 inches deep. The forward end 23 of the petal tip has a 0.030 inch radius of curvature.

The spacing X between the forward ends 23 of opposed petals 25 manufactured in accordance with the preferred method of my invention is shown in 7-1, with 7-2 showing the measured result without the addition of moisture.

It will be observed that upon initial manufacture, the inter-petal gap spacing, which is an indication of the degree of petal tip openness, is initially reduced by the addition of moisture. However, more significantly, is what occurs during storage of the applicator assembly prior to use. In both instances, the measured distance or gap X becomes relatively stable after about two days. However, the gap X achieved by the practice of the instant invention is in the order of 0.143 inches, whereas the gap resulting from an applicator tube in which the addition of moisture is not presented prior to fabrication is in the order of 0.20 inches. That is, there is an approximately 30 per cent reduction in this gap spacing, which is naturally indicative of a substantial improvement in tampon tip stability.

Accordingly, my invention grammatically provides a convenient method for increasing the stability of the petals forming the closure end of a cardboard tampon applicator. Although a specific embodiment has been disclosed, variations thereto may be made in accordance with the other desired product characteristics and parameters. Accordingly, the particulars of that embodiment is not intended to be construed as limiting the scope of the invention, which is defined by the following claims:

What is claimed is:

1. A method of forming a cardboard tampon applicator including a barrel member adapted to contain a tampon pledget therein, and having a dome-shaped tip forward end formed of a plurality of curved petals through which the tampon pledget is ejected, comprising the steps of:
   forming a cardboard cylinder having an initially fully opened forward end, with a plurality of petals at the terminus of the forward end,
   spraying moisture over at least the forward end and a major portion of one or more surfaces of each of the petals, and
   curving the sprayed portions of the petals radially inward while heating to collectively form and maintain the generally dome-shaped forward end.

2. The method of forming a cardboard tampon applicator as set forth in claim 1, wherein said barrel member is convolutely formed.

3. The method of forming a cardboard tampon applicator as set forth in claim 1, wherein the radially inward curving of the petals comprises urging the petals against a heated concave die.

4. The method of forming a cardboard tampon applicator as set forth in claim 3, wherein the heated concave die is at a temperature in the order of 350 degrees fahrenheit.

5. The method of forming a cardboard tampon applicator as set forth in claim 1, wherein the moisture sprayed on the petals is primarily water.

6. The method of forming a cardboard tampon applicator as set forth in claim 5 wherein said barrel member is convolutely formed.

7. The method of forming a cardboard tampon applicator as set forth in claim 5, wherein the water is at temperature between 75 to 85 degrees fahrenheit.

8. The method of forming a cardboard tampon applicator as set forth in claim 4, wherein between approximately 0.02 to 0.03 grams of water is sprayed onto the inner surfaces of the petals of each barrel.

9. The method of forming a cardboard tampon applicator as set forth in claim 4, wherein,
   the moisture sprayed on the petals is primarily water, and
   the spraying of water on the petals prior to their being heat set into the domed configuration effectively maintains a desired domed configuration of the petals during prolonged periods between manufacture and use.

10. A method of forming a cardboard tampon applicator including a barrel member adapted to contain a tampon pledget therein, and having a curved dome-shaped forward end formed of a plurality of petals through which the tampon pledget is ejected, each petal having an inner curved surface and an outer curved surface, the method comprising the sequential steps of:
    forming a cardboard cylinder having an initially fully opened forward end, with a plurality of circumferentially spaced-apart petals at the terminus of the forward end;
    spraying water at a temperature between about 75 to 85 degrees fahrenheit and in an amount between about 0.020 to 0.030 grams over at least the forward end and a major portion of at least one of the inner and outer surfaces of each of the petals; and
    curving the sprayed portions of the petals radially inward to collectively form the curved dome-shaped forward end by urging the petals against a concave die heated to a temperature about 350 degrees fahrenheit, whereby said dome-shaped forward end is maintained.

11. The method of forming a cardboard tampon applicator as set forth in claim 10, wherein the water is sprayed over the forward end and a major portion of both the inner and outer surfaces of each of the petals.

* * * * *

UNITED STATES PATENT AND TRADEMARK OFFICE
CERTIFICATE OF CORRECTION

PATENT NO.   : 5,290,501
DATED        : March 1, 1994
INVENTOR(S)  : Allan W. Klesius It is certified that error appears in the above—identified patent and that said Letters Patent is hereby corrected as shown below:

Column 2, line 37, after "petals," insert --also--.

Column 2, line 38, delete "also".

Column 4, line 3, after "variations" insert --in the location--.

Column 4, line 4, delete "in the location".

Signed and Sealed this

Fifth Day of July, 1994

Attest:

BRUCE LEHMAN

*Attesting Officer*  *Commissioner of Patents and Trademarks*